US00PP12712P2

(12) United States Plant Patent
Oudshoorn

(10) Patent No.: US PP12,712 P2
(45) Date of Patent: Jun. 18, 2002

(54) PAPAVER PLANT NAMED 'PINK RUFFLES'

(75) Inventor: Herbert Oudshoorn, Rypwetering (NL)

(73) Assignee: Future Plants V.O.F., Noordwijk (NL)

( * ) Notice: Subject to any disclaimer, the term of this patent is extended or adjusted under 35 U.S.C. 154(b) by 35 days.

(21) Appl. No.: 09/624,465

(22) Filed: Jul. 24, 2000

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Papaver plant named 'Pink Ruffles', characterized by its upright and compact plant habit; dark green leaves; vigorous growth habit; freely flowering habit; and pink petals with fringed margins.

2 Drawing Sheets

BACKGROUND OF THE INVENTION

The present Invention relates to a new and distinct cultivar of Papaver plant, botanically known as *Papaver orientale* L., commercially referred to as Oriental Poppy, and hereinafter referred to by the cultivar name Pink Ruffles.

The new Papaver is a product of a planned breeding program conducted by the Inventor in Rypwetering, The Netherlands. The new Papaver originated from a self-pollination made by the Inventor of the Papaver cultivar Garden Glory, not patented. The new Papaver was selected by the Inventor in 1996 from the resultant progeny on the basis of its compact plant size, floriferousness and vigor.

Asexual reproduction of the new cultivar by cuttings taken at Rypwetering, The Netherlands, has shown that the unique features of this new Papaver are stable and reproduced true to type in successive generations.

SUMMARY OF THE INVENTION

Plants of the cultivar Pink Ruffles have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Pink Ruffles'. These characteristics in combination distinguish 'Pink Ruffles' as a new and distinct cultivar:

1. Upright and compact plant habit.
2. Dark green leaves.
3. Vigorous growth habit.
4. Freely flowering habit.
5. Pink petals with fringed margins.

Plants of the cultivar Pink Ruffles differ from plants of the parent cultivar, Garden Glory in the following characteristics:

1. Plants of the new Papaver are more compact and shorter than plants of the cultivar Garden Glory.

2. Plants of the new Papaver have darker green and glossier leaves than plants of the cultivar Garden Glory.

3. Plants of the new Papaver are more vigorous than plants of the cultivar Garden Glory.

4. Plants of the new Papaver are more freely flowering than plants of the cultivar Garden Glory.

5. Petals of the new Papaver have fringed margins whereas petals of the cultivar Garden Glory have entire margins.

Plants of the cultivar Pink Ruffles can be compared to plant of the cultivar Kleine Tanzerin. Plants of the cultivar Pink Ruffles differ from plants of the cultivar, Kleine Tanzerin in the following characteristics:

1. Plants of the new Papaver are sturdier than plants of the cultivar Kleine Tanzerin.

2. Petals of plants of the new Papaver are more intense pink in color than petals of the cultivar Kleine Tanzerin.

3. Petals of the new Papaver have fringed margins whereas petals of the cultivar Kleine Tanzerin have entire margins.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Papaver.

The photograph at the top of the first sheet comprises a side perspective view of typical flowering plants of 'Pink Ruffles' grown in a container that were about 25 weeks old.

The photograph at the bottom of the first sheet is a close-up view of a typical leaf of 'Pink Ruffles'.

The photograph at the top of the second sheet is a close-up view of typical flower buds and open flower of 'Pink Ruffles'.

The photograph at the bottom of the second sheet is a close-up view of a typical flower of 'Pink Ruffles'.

DETAILED BOTANICAL DESCRIPTION

In the following description, color references are made to The Royal Horticultural Society Colour Chart except where general terms of ordinary dictionary significance are used. Plants grown in containers were used for the following description. Plants were grown under field conditions which closely approximate commercial production conditions during the spring and summer in Rypwetering, The Netherlands and were about 25 weeks old.

Botanical classification: *Papaver orientale l.* cultivar Pink Ruffles.

Parentage: Self-pollination of *Papaver orientale l* . cultivar Garden Glory, not patented.

Propagation:

Type cutting: Cuttings.

*Time to develop roots.*—Cuttings harvested in October develop roots in March in the Northern Hemisphere.

*Root description.*—Fleshy.

Plant description:

*Form.*—Robust hispid perennial flowering plant; mostly upright and somewhat outwardly arching; triangular. Basally branching, rosette, flowering stems arise from the base. Appropriate for 2-liter containers.

*Crop time.*—About 25 weeks are required to produce finished flowering plants in 2-liter containers.

*Plant height.*—About 55 cm.

*Plant diameter.*—About 60 cm.

*Vigor.*—Vigorous.

*Foliage description.*—Leaves simple, generally symmetrical and long persisting. Arrangement: Alternate. Shape: Lanceolate, pinnately and deeply dissected. Length: About 32 cm. Width: About 8 cm. Leaf segment shape: Narrowly oblanceolate. Leaf segment apex: Acuminate to acute. Leaf segment base: Acuminate to cuneate. Leaf segment margin: Biserrate. Texture: Slightly rugose; both surfaces covered with pale gray to greenish white hairs, about 2 mm in length. Color: Young foliage, upper surface: 137A. Young foliage, lower surface: 138B. Mature foliage, upper surface: 137A; veins, 139C. Mature foliage, lower surface: 138B; veins, 139C.

Flower description:

*Flower type and habit.*—Large-sized single flowers; flowers face outward to upright. Flowers not persistent. Freely flowering; typically about seven flowers and flower buds per plant at one time.

*Natural flowering season.*—Late spring.

*Fragrance.*—None detected.

*Flower longevity on the plant.*—About three to five days.

*Flower size.*—Diameter: About 15 cm. Depth (height): About 6 cm.

*Flower buds* (*before showing color*).—Length: About 3.5 cm. Diameter: About 2.3 cm. Shape: Oblong. Aspect: Nodding. Texture: Pubescent, covered with pale gray to greenish white hairs about 2 mm in length. Color: 141C to 141D. Rate of opening: About four weeks from visible bud to open flower.

*Corolla.*—Arrangement/appearance: About seven petals forming a cup-shaped corolla. Petal length: About 6 cm. Petal width: About 6 cm. Petal shape: Deltoid to somewhat orbicular. Petal apex: Rounded. Petal margin: Deeply incised; fringed appearance. Petal texture: Smooth, satiny. Color: Petal, upper surface, when opening: 39B; base, 50A. Petal, lower surface, when opening: 39B; base, 46A. Petal, upper surface, fully opened: 39B; base, 50A. Petal, lower surface, fully opened: 39B; base, 50A.

*Calyx.*—Sepal arrangement: Three, irregulary spaced. Calyx length: About 8 cm. Calyx width: About 8 cm. Sepal shape: Lanceolate. Sepal apex: Acuminate. Margin: Deeply incised. Texture: Slightly rugose. Color: Upper surface: 192A to 193C; margins, 135A to 137A. Lower surface: 138B to 145C; margins, 137A to 138A.

*Peduncles.*—Length: About 55 cm. Diameter: About 6 mm. Strength: Good, supports weight of flower. Texture: Densely covered with pale gray to almost white hairs, about 3 mm in length. Color: 141C to 141D.

*Reproductive organs.*—Stamens: Quantity: Numerous, typically more than 200. Anther shape: Basifixed. Anther length: About 3 mm. Anther color: 202A. Pollen amount: Scarce. Pistils: Quantity: One. Pistil length: About 1.5 cm. Stigma color: 200A to 200B.

*Seed description.*—Length: About 0.8 mm. Diameter: About 0.8 mm. Color: Dull, dark bluish gray.

Disease resistance: Plants of the new Papaver have been noted to be resistant to pathogens common to Papaver.

Weather tolerance: Plants of the new Papaver are tolerant to rain and wind.

It is claimed:

1. A new and distinct cultivar of Papaver plant named 'Pink Ruffles', as illustrated and described.

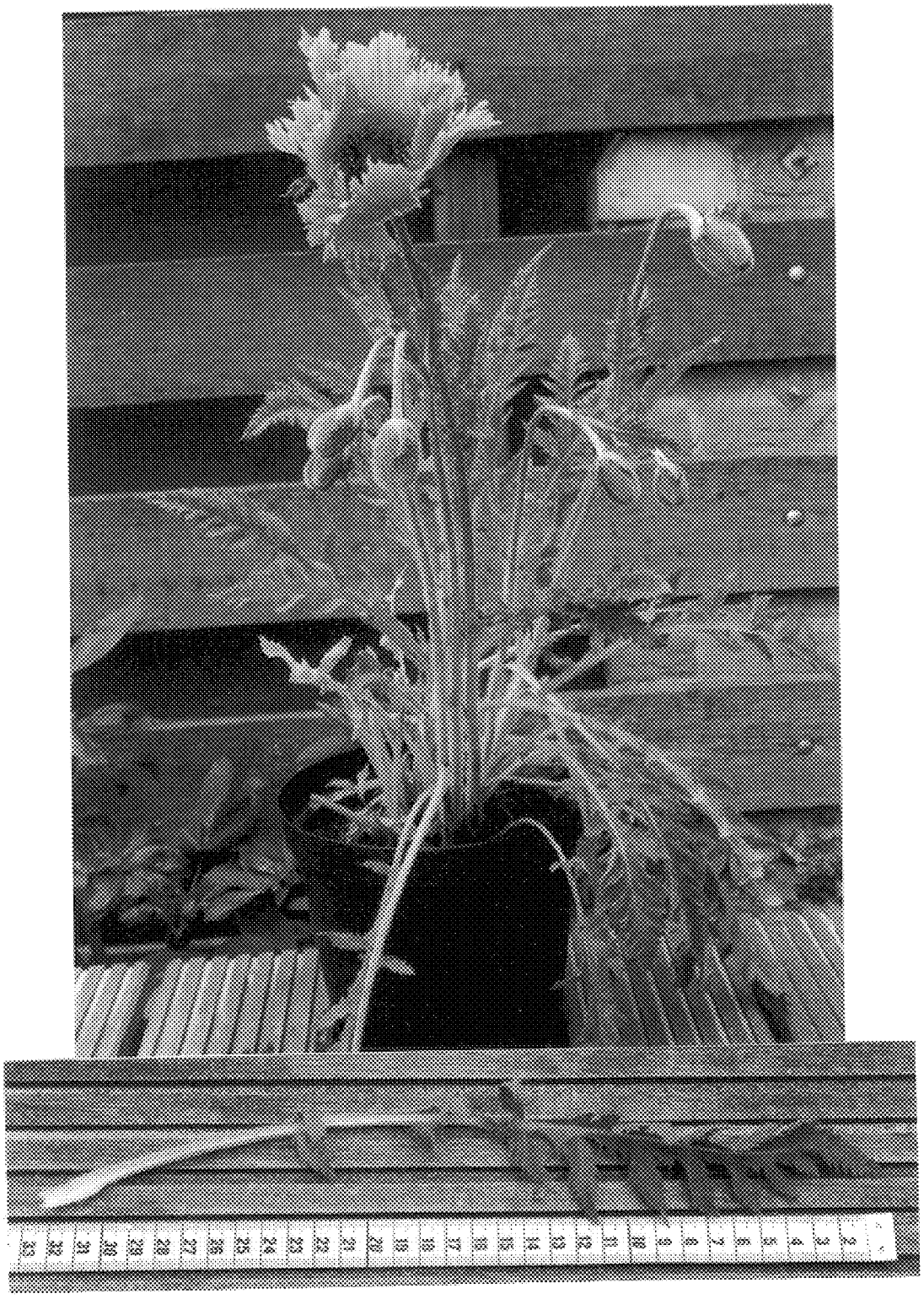

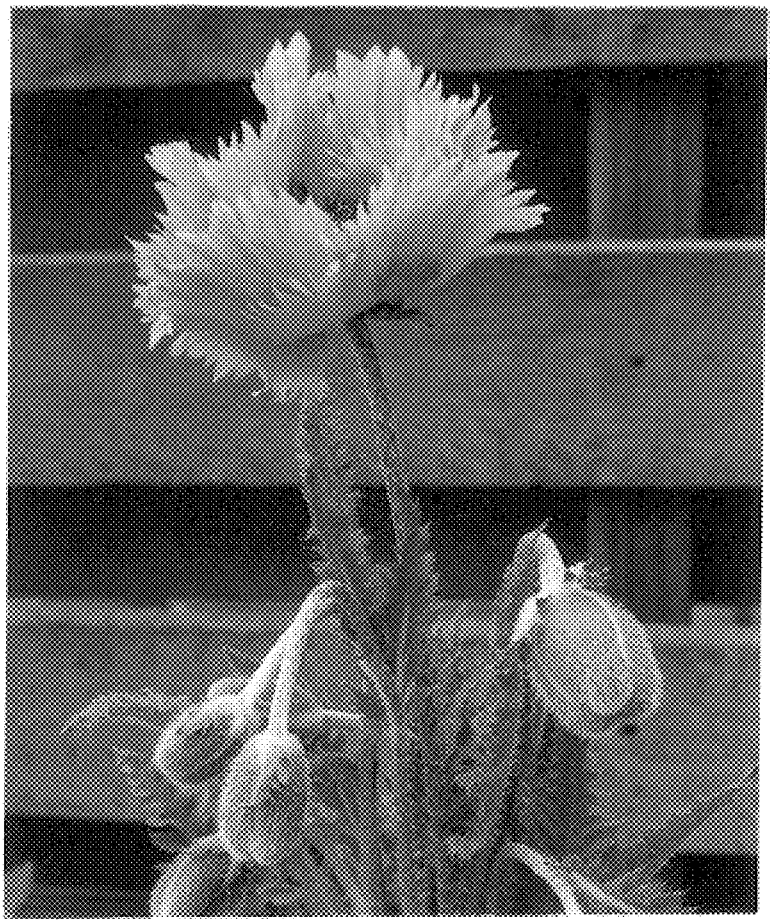
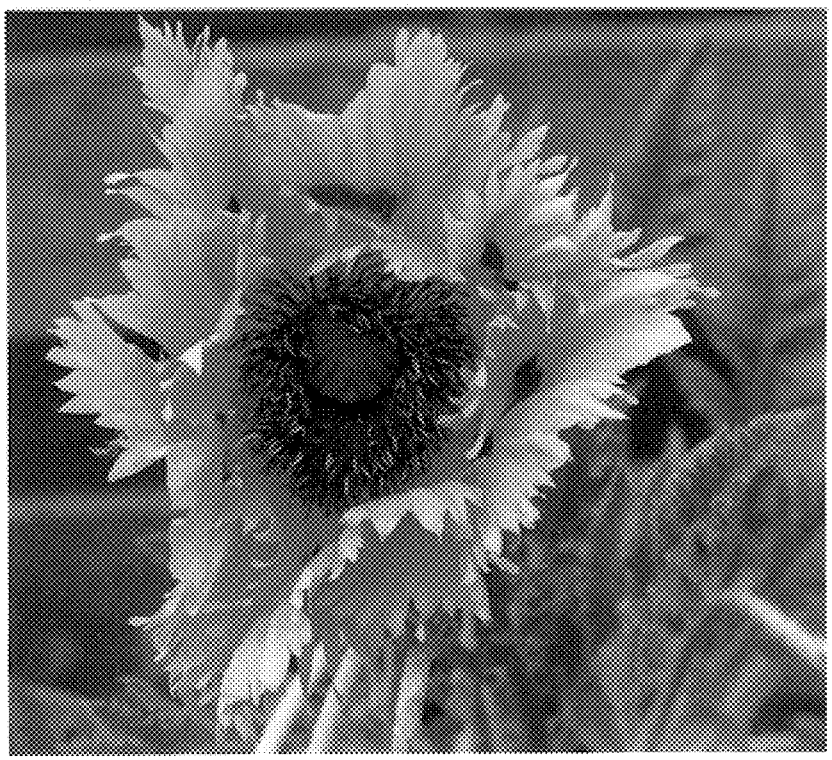

* * * * *